(12) United States Patent
Margiotta

(10) Patent No.: US 6,274,167 B1
(45) Date of Patent: Aug. 14, 2001

(54) TOPICAL ANESTHETIC PATCH

(76) Inventor: Vincent Margiotta, 43 Geraldine Rd., Englewood Cliffs, NJ (US) 07632

( * ) Notice: Subject to any disclaimer, the term of this patent is extended or adjusted under 35 U.S.C. 154(b) by 0 days.

(21) Appl. No.: 09/662,169

(22) Filed: Sep. 14, 2000

(51) Int. Cl.$^7$ ............................. A61K 9/70; A61L 15/16
(52) U.S. Cl. ..................... 424/449; 424/447; 424/443; 424/446
(58) Field of Search ............................ 424/449, 447, 424/443, 446

(56) References Cited

U.S. PATENT DOCUMENTS 4,992,508 * 2/1991 Vishnupad et al. ................. 524/601
5,641,507 * 6/1997 Devillez .............................. 424/443

\* cited by examiner

Primary Examiner—Thurman K. Page
Assistant Examiner—Rachel M. Bennett

(74) Attorney, Agent, or Firm—Donald R. Heiner

(57) ABSTRACT

A pre-vaccination or pre-procedural topical anesthetic patch which functions not unlike a nicotine patch and which is essentially a round Band-Aid® (trademark) containing a topical anesthetic. The Band-Aid® anesthetic carrying device may be of any shape or size. It is applied to a persons skin at a site where a needle is to be inserted such that the site will have a topical anesthetic applied. When the Band-Aid® is removed from the site prior to a needle being inserted a visible delineation of a target area is visible on the skin. That is, that side of the Band-Aid® which contacts the skin will contain a dye, of any color, although preferably red, in the form of a circle or any other geometric shape, smaller than the diameter or size of the Band-Aid®, whereby when the Band-Aid® is removed the dye will leave a mark at the site which is the "target" area. Particularly important is the fact that once the Band-Aid® or patch is removed, prior to a needle being inserted, the target area or bull's eye or a red circle or any other color circle or geometric shape will be left on the skin which clearly delineates where the anesthetic is and, therefore, where the needle should be inserted.

8 Claims, 3 Drawing Sheets

TOPICAL ANESTHETIC PATCH

BACKGROUND OF INVENTION

1. Field of the Invention

The present invention generally involves the field of technology pertaining to an anesthetic patch, principally used for babies and small children, but which may be used by others, wherein the device is essentially a common everyday sold over-the-counter preferably round Band-Aid® (trademark) containing a topical anesthetic. The device is placed on a persons skin at a site where a needle is to be inserted such that the area will have a topical anesthetic applied or anesthetic effect. Obviously, the device is applied to the skin in advance of the needle insertion. It should be emphasized that both the Band-Aid® or any other type of bandage material as well as the anesthetic agents are well known and are presently approved for over-the-counter sale.

It should be obvious that the anesthetic carrying material may be something other than a Band-Aid® or bandage but can be of other material that will not only carry the anesthetic but will also adhere to a persons skin.

For purposes of further discussing this device the Band-Aid® or bandage or skin contacting anesthetic carrying material will be referred to as an adhesive patch. It is this adhesive patch that will carry any type of topical anesthetic that will prove satisfactory for this purpose and will also carry a dye material on that side of the adhesive patch that coacts with the skin. When the adhesive patch is removed, prior to a needle being inserted, it will therefore leave a visible delineation of a "target" area which may be of any geometric shape, although preferably circular, and of any color, preferably red, which clearly marks the spot where a needle etc. is to be inserted.

This adhesive patch further comprises a pad of absorbent material, such as but not limited to cotton, which contains both active and inactive ingredients. That portion of the absorbent pad to be placed over the site to be injected or punctured will be somewhat smaller in size than the overall size of the adhesive patch.

It is anticipated that the active ingredient indicated above will be benzocaine and the inactive ingredient indicated above will be glycerin or water or any other benign vehicle. These can be in varying proportions depending upon the age of the recipient.

Any well known dye such as red food dye may be used on the skin side of the adhesive patch to mark the spot to be penetrated. It should also be obvious that the active and inactive ingredients can be other then benzocaine and glycerin.

2. Description of the Prior Art

A search of the prior art has uncovered the following patents:U.S. Patent to E. Blank, 1,682,657; Patel, 4,162,673; Barrett, 4,243,035; Haber, 4,799,926; Grinwald, 5,003,987; Stalcup, et al, 5,112,297; Atef, 5,833,649; and Steinhardt, et al, 5,902,669.

The patent to Blank, 1,682,657 is of little interest in that in essence it is really not much more than a brush or any other type applicator and does not comprise an adhesive patch having absorbent cotton and dye.

The patent to Patel, 4,162,673 is simply a method of testing the position of a needle assembly in the epidural space of a patients body.

Of some general interest is the Patent to Barrett 4,243,035 which is an integral hypodermic syringe and antiseptic dispenser. This would be likened to a pencil having lead at one end and an eraser at the other. This invention is clearly not an adhesive patch soaked with anesthesia and dye which delineates a target area.

Not unlike the Barrett patent discussed above is the patent to Haber 4,799,926 which in fact cites the Barrett patent. These two patents are seen as being quite similar to each other. This patent is probably even closer to the analogy of a pencil having lead at one end, an eraser at the other, especially as seen in FIG. 3. In this patent the swab 10 is located at and moved around the targeted tissue area 20 of the patient so that an adequate amount of medication will be applied from the swab to the target site. It is after that procedure that the needle is exposed for administering an injection at the target site.

The Grinwald patent, 5,003,987 entitled "METHOD AND APPARATUS FOR ENHANCED DRUG PERMEATION OF SKIN" requires removal of the outermost layers of the skin by "gentle abrasion" and then measuring the change in the electrical resistance or impedance of the skin as the outmost layers of the skin are removed.

Collectively, the patents to Stalcup, et al, 5,112,297; Atef, 5,833,649; and, Steinhardt, et al, 5,902,669 are of general interest only and fail to disclose the invention described herein.

SUMMARY OF INVENTION

According to the present invention there is provided an adhesive patch, not unlike current nicotine patches, comprising an adhesive bandage backing, preferably of plastic, but possibly of other materials, which serves as the backing for the adhesive patch of this invention. On that side of the adhesive patch is a band of gauze or cotton or any other suitable absorbent material which adheres to the adhesive bandage or patch by any suitable means.

One side of the gauze pad or cotton pad maybe impermeable which is the side that adheres to the adhesive bandage backing. The other side of the pad, that is, the side which will contact the skin, is absorbent.

A quantity of the benzocaine solution is then applied to the absorbent pad and surrounding that sample or supply of benzocaine solution is a food dye or the like and in a preferred embodiment it is that circular shaped dye color the inside of which forms the target area for a needle.

In an alternate embodiment the benzocaine and dye are mixed together and again applied to the absorbent gauze pad.

In either the preferred embodiment or the alternative embodiment when the adhesive bandage is removed it will leave a target area for a needle.

For both the preferred and alternate embodiment the entire device is protected with a plastic or foil strip such that the adhesive patch is kept moist at all times. The entire device is therefore packaged as sterile as are other adhesive bandages.

It is therefore an object of the present invention to provide an anesthetic patch principally used for but not limited to babies and small children.

It is another object of the invention to provide an anesthetic patch which is an adhesive patch to be placed on a person's skin at a site where a needle is to be inserted.

It is a further object of the invention to provide such a patch comprising a pad of absorbent material such as cotton containing a topical anesthetic comprising both active and inactive ingredients.

It is yet a further object of the invention to provide such a patch wherein the active and inactive ingredients are preferably benzocaine and glycerine respectively.

It is still a further object of the invention to provide such a patch wherein the active and inactive ingredients may be of varying proportions depending upon the age of the recipient.

It is still a further object of the invention to provide such a patch wherein a skin side of the patch further contains any suitable dye material such that the site on the skin to be penetrated marks the spot of needle insertion.

It is still a further object of the invention to provide such a patch wherein a quantity of benzocaine solution is applied to the absorbent pad and surrounding that quantity of benzocaine is the dye preferably of circular shape.

It is still a further object of the invention to provide such a patch wherein the benzocaine an dye are mixed together and applied to the absorbent gauze pad.

These and further objects, features and advantages of the invention shall become apparent form the following detailed description of a preferred embodiment thereof when taken in conjunction with the drawings wherein like reference characters refer to corresponding parts in the several views.

DETAILED DESCRIPTION OF THE PREFERRED EMBODIMENT

Figure 1:
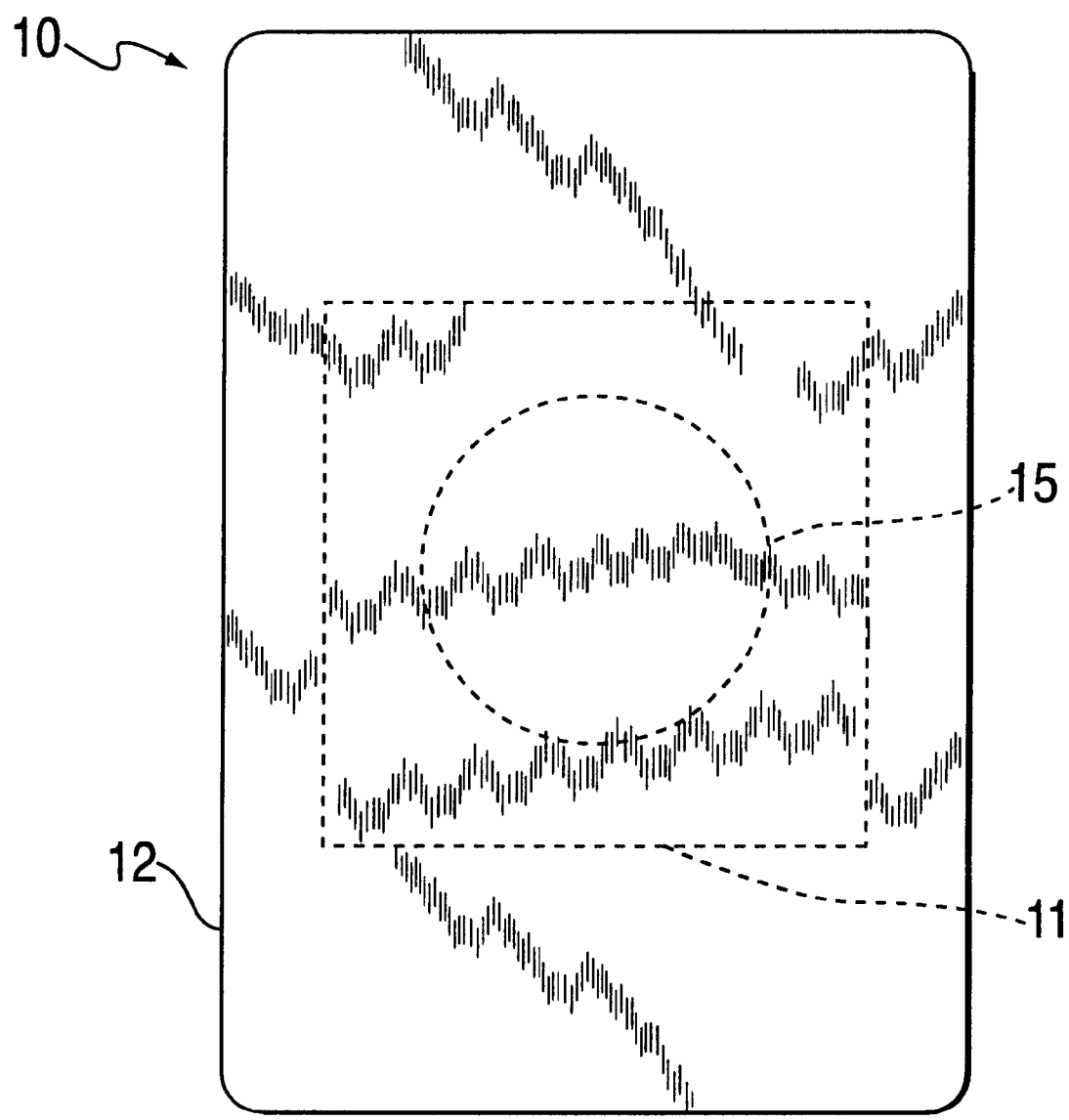
FIG. 1 is a plan view of the patch showing the non-skin contacting side of the adhesive patch.

An anesthetic adhesive patch which may be applied to a persons skin by anyone including the person themselves, a parent, pediatrician, etc. at the site where a needle is to be inserted, for any reason, and which contains a light topical anesthetic solution carried by an absorbent material, such as cotton, and which contains both active and inactive ingredients for the purpose of applying a light anesthetic to the skin will now be described with reference to the drawings.

The adhesive patch is shown generally at 10 having a gauze pad 11 attached to one side of a backing 12, preferably of plastic, and wherein the gauze pad can have an impermeable side 13 coacting with backing 12 and an absorbent top side 14 which coacts with a wearer's skin.

A benzocaine solution 15 of an appropriate percentage of concentration of benzocaine, usually, but not necessarily, in the range of 10%–20%, is applied to gauze pad 11, and, surrounding that portion 15 of gauze pad 11 containing the solution, is a dye 16 of any suitable color, but preferably red, which, in using the adhesive patch 10, as will be more fully described below, will leave a demarcation zone or target area on the skin when the adhesive patch is removed. This target area is where a needle will be inserted.

The dye is applied to the gauze pad by any suitable means and, while shown as circular in the drawings, may be of any other convenient geometric shape having a non-colored producing center.

As an alternative, the benzocaine solution and dye may be mixed together and applied to the absorbent gauze pad 11.

Again, when the adhesive patch is removed from the skin, a target area will be left on the skin leaving a geometric shaped area with a colored middle.

The dye is generally and commonly referred to as FD&C #40 (red) although other colors may be used.

The entire patch described above is preferably covered with a plastic or foil strip to retain moisture and retard evaporation. The entire patch is therefore packaged as sterile as are other over-the-counter adhesive bandages.

The benzocaine solution 15 shown on the gauze pad 11, and preferably of a 10% solution, comprises well known ingredients benzocaine in a crystalline form, polyethylene glycol which acts as a solvent for the crystalline benzocaine, sterile water which is a vehicle for the color, FD&C #40 common food dye and possibly sorbitol preservative.

If the benzocaine solution is to be 10% then 1 gram of crystalline benzocaine (solute) is dissolved into 10 ml of the solvent (polyethylene glycol). If a 20% solution is desired then 2 grams of solute (benzocaine) is dissolved into the same quantity (10 ml) of the polyethylene glycol solvent. Added to the foregoing to yield a final volume of 10 ml is 0.5 ml of the sterile water and 0.5 ml of FD&C #40.

It should be understood that the concentration of the solvent mixture components may be changed, as required, depending upon the desired effect of demarcating the area. Increasing the amount of dye will increase the intensity and duration ofthe demarcated or target area. However an increase or decrease in any one component will need to be compensated for with a corresponding increase or decrease in one or more of the other components to maintain proper desired stoiciometric percentages.

In addition to the preferred embodiments discussed above there are two other embodiments well within the contemplation of the invention and shown in the drawings and generally discussed above. Both of these other embodiments comprise the backing 12, gauze pad 11 and the dye 16. Still added to the gauze pad 11 is the benzocaine solution generally shown at 15.

Figure 2:
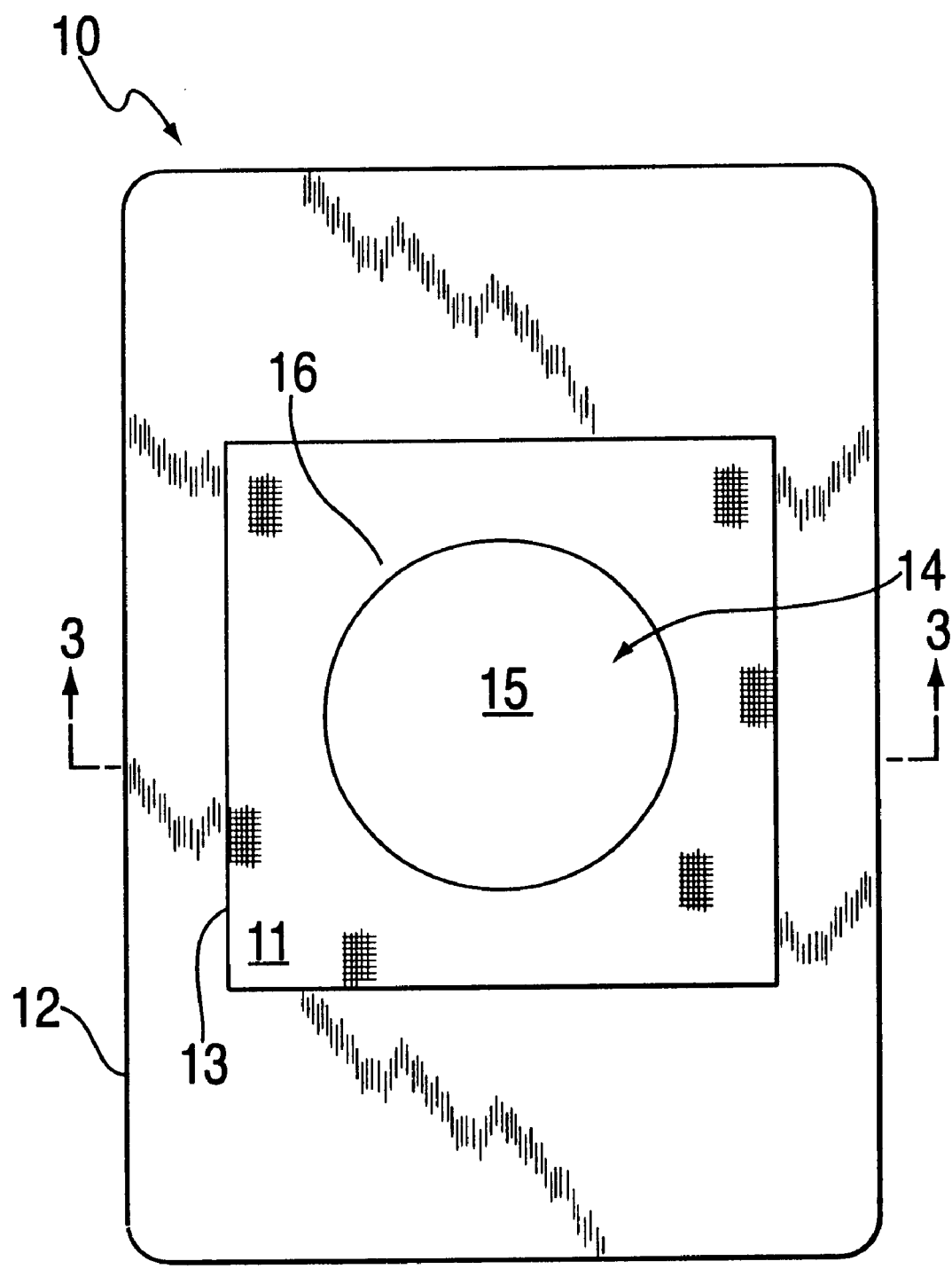
FIG. 2 is a view showing the reverse side which is the skin contacting side.
Figure 4:
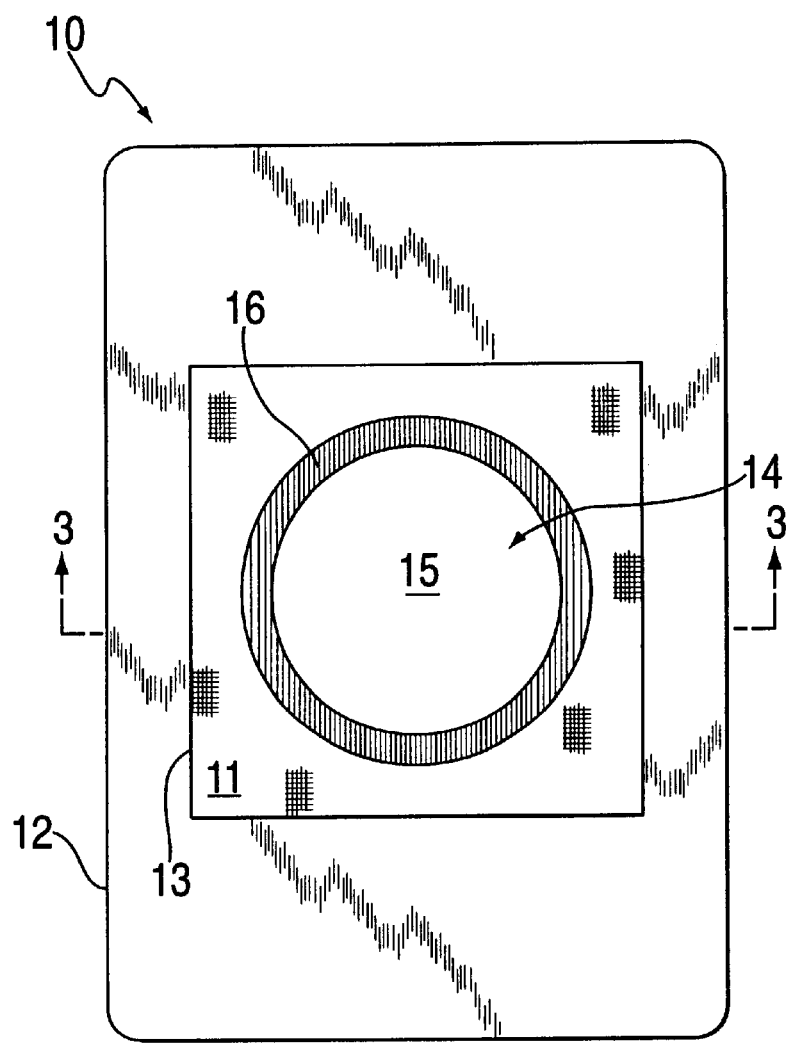
FIG. 4 is a view similar to FIG. 2 but showing dye material surrounding a pad of absorbent material.
Figure 3:
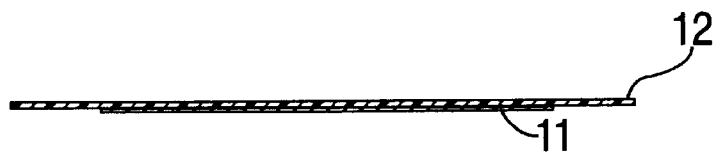
FIG. 3 is a cross sectional view taken on line 3—3 of FIG. 2.

In both of these additional embodiments the dye shown as 16 in FIGS. 2 and 4 would preferably take the shape of a washer such as shown as item 16 in FIG. 4.

In one of these embodiments the washer or ring shaped dye element is attached directly to backing 12 and gauze pad 11 is placed over the dye ring with the gauze pad 11 being of a smaller size such that the dye will still contact the skin thereby leaving the target zone on the skin. At the same time, obviously, the gauze pad containing the benzocaine solution will still anesthesize the skin.

In yet another embodiment the placement ofthe dye ring and gauze ring are reversed from that discussed above. That is, the gauze pad is attached to the adhesive backing and the washer shaped dye ring, having a diameter less than the size of the gauze pad, is placed on top of the gauze pad. As can readily be seen the skin will still be anesthesized and a dye mark will still be left on the skin.

It should be obvious that in either of the above 2 mentioned embodiments the dye carrying element can be triangularly shaped, square shaped, rectangular shaped, or any other convenient geometric shaped.

In operation, the adhesive patch is removed from its protective devise such as the plastic or foil strip, and is placed on a person's skin, at a predetermined time, and most likely at a predetermined place, with the absorbent gauze pad contacting the skin. The adhesive bandage backing adheres to the skin. At this time the skin area under the gauze pad will come into contact with the Topical Anesthetic Agent Solution. When a needle is to be inserted into the person at the site the patch is removed leaving a demarcated or target area of dye, of any geometric shape, thereby indicating the site for the needle to be inserted. When the patch is removed from the skin it is disposed of.

Though the invention has been described and illustrated with reference to a prefer embodiment thereof, those skilled in the art will appreciate that various changes and modifications in shape, size, composition, and arrangement of parts may be resorted to without departing from the spirit of the invention or scope of the subjoined claims.

What is claimed:

1. An anesthetic carrying adhesive patch attachable to a persons skin comprising:
   (a) a backing;
   (b) a pad attached to one side of said backing;
   (c) an anesthetic solution applied to said pad; and,
   (d) dye operatively associated with said pad whereby when said patch is applied to a persons skin and then removed the skin is anesthesized and a target area for reception of a needle is delineated by said dye operatively associated with said pad.

2. The anesthetic carrying adhesive patch of claim 1 wherein said backing is plastic.

3. The anesthetic carrying adhesive patch of claim 2 wherein said pad is gauze.

4. The anesthetic carrying adhesive patch of claim 3 wherein said anesthetic solution is a benzocaine solution.

5. The anesthetic carrying adhesive patch of claim 4 wherein said anesthetic solution contains both active and inactive solutions.

6. The anesthetic carrying adhesive patch of claim 5 wherein said gauze pad has an impermeable side coacting with said backing and an absorbent top side which coacts with a persons skin.

7. The anesthetic carrying adhesive patch of claim 6 wherein said benzocaine and said dye are mixed together and applied to said gauze pad whereby when said adhesive patch is removed from a persons skin a target area is left on anesthesized skin.

8. The anesthetic carrying adhesive patch of claim 7 wherein said benzocaine solution comprises benzocaine in a crystalline form, polyethylene glycol, sterile water and sorbitol preservative.

* * * * *